United States Patent [19]
Poole

[11] Patent Number: 6,048,570
[45] Date of Patent: Apr. 11, 2000

[54] EVIDENCE-PRESERVING CONTAINER AND METHOD OF USING THE CONTAINER

[76] Inventor: Harvey D. Poole, 8530 Bentwood Dr., North Charleston, S.C. 29406

[21] Appl. No.: 09/138,819

[22] Filed: Aug. 21, 1998

[51] Int. Cl.[7] .................................................. A61B 5/117
[52] U.S. Cl. .............................. 427/1; 427/145; 427/261; 427/258; 427/337
[58] Field of Search ................................ 427/1, 145, 261, 427/258, 255.6, 337

[56] References Cited

U.S. PATENT DOCUMENTS

| | | | |
|---|---|---|---|
| 4,297,383 | 10/1981 | Bourdon | 427/1 |
| 4,471,869 | 9/1984 | Hasenfus | 206/1.7 |
| 4,700,657 | 10/1987 | Butland | 427/1 |
| 5,266,112 | 11/1993 | Crosbie | 427/1 |

*Primary Examiner*—Janyce Bell
*Attorney, Agent, or Firm*—B. Craig Killough

[57] ABSTRACT

An carrying container and method for holding and transporting evidence, the case having a base portion and a cover portion and both vertically and horizontally adjustable securing means. The base portion has multiple support bars upon which slidably affixed support racks or U-clamps are positioned. The adjustable support racks or clamps position the item to be carried and securely hold the item placed therein. A storage compartment may also be incorporated. The container has a port or vent through which fingerprint dust fixative can be injected to fix fingerprint dust that has been applied to the item so that latent fingerprints can be identified. The container protects the item from damage and minimizes physical contact with the item and thus protects and preserves any latent fingerprints that may exist on the item.

18 Claims, 3 Drawing Sheets

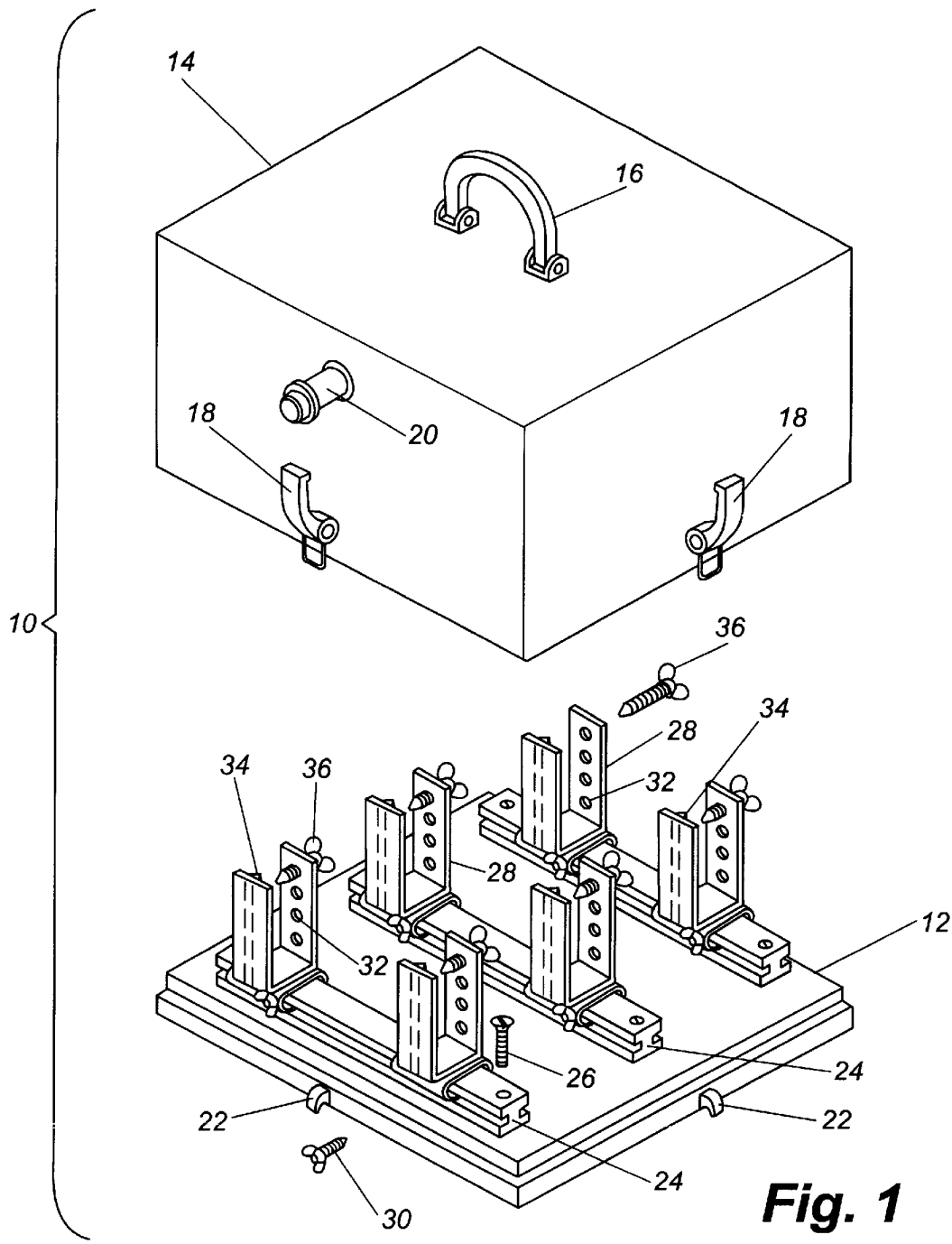
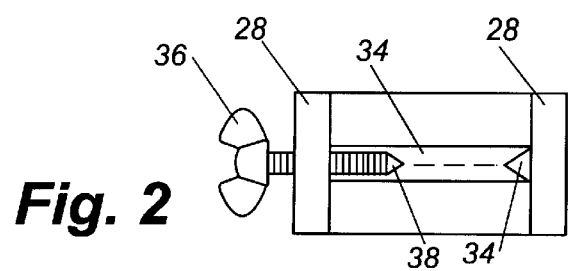
Fig. 1
Fig. 2

EVIDENCE-PRESERVING CONTAINER AND METHOD OF USING THE CONTAINER

TECHNICAL FIELD

This invention relates to the field of containers, and more particularly, to a container that will transport police evidence with minimal physical contact, and which allows the evidence to be processed for latent fingerprints inside the container.

BACKGROUND OF THE INVENTION

One of the major technical problems involved in any criminal investigation is the correct handling of evidence - actually the need for avoiding handling of the items found at the site of a crime that may be connected to the crime, or which otherwise may be used to identify the perpetrator of the crime. The need for minimal handling of the item found is to prevent obliteration or confusion of fingerprints that may exist on the article of evidence.

Fingerprinting is most frequently performed by dusting the item of evidence with latent print powder, then applying a fixative to the dusted item. The fingerprints then become visible, and can be photographed and lifted from the item using fingerprint lifting tape, and placed on a card with an appropriately colored background for later use as evidence. On large items, such as automobiles, this dusting is usually done at the crime scene. Smaller, transportable items, such as a handgun found at the site of a crime, are typically placed in a plastic bag, cardboard box, or similar container, and taken to a crime lab for fingerprint analysis. This procedure involves the handling of the item at least twice: first, as the item is picked up and placed into a bag or other container for transport, and secondly, as the item is removed from the container at the lab. Subsequent handling may occur as the article is moved about at the lab, including movement during processing. Boxes and bags used to carry the items frequently smudge or otherwise destroy the fingerprints.

Although law enforcement individuals and technicians wear gloves when performing these operations, gloves typically leave marks, and may smudge existing fingerprints. Such handling can cause problems, since, before dusting, it cannot be ascertained where critical fingerprints may exist.

Rigid carrying cases are known, including cases for carrying firearms, but none have the combination of support/contact points that are adjustable both vertically and horizontally and that also minimize surface contact with the gun while it is in the case. Lauve, U.S. Pat. No. 5,454,931 discloses a rack for transporting guns that has a series of supports for the gun base, and clips to hold and support the barrels. Hagemann, et al., U.S. Pat. No. 5,678,686 discloses a rigid case into which a single rifle is placed. The rifle is supported within the case by cradles into which it is fastened.

SUMMARY OF THE INVENTION

The present invention reduces the number of times an item of evidence must be handled during the fingerprinting process. The present invention provides a rigid case having a base portion and a cover portion which can be clipped to each other for carrying. The base portion has several support bars upon which slidably affixed support racks are positioned. The support racks have openings on one side, through which support thumb screws can be adjustably placed to vertically position the item and selectively provide the required width of the opening, to securely hold an item placed therein. The case has a port or vent through which the fixative material may be applied to fix the dust which is used to coat the item for identification of latent fingerprints. Accordingly, it is an object of the present invention to provide a case that protects the collected evidence from damage, and minimizes physical contact with the evidence, through a system of adjustable securing at contact points. It is a further object of the invention to provide such a case that will allow an item placed inside to have the fingerprint dust fixed within the container without the necessity of removing the item from the case until the fixing of the latent fingerprints is complete. After the dust is fixed, the cover of the container can be removed for photographing and lifting of prints, with minimal physical contact with the item of evidence.

BRIEF DESCRIPTION OF DRAWINGS

FIG. 1 is a partially exploded perspective drawing of the evidence preserving carrier of the present invention.

FIG. 2 shows a simplified top view of a detail of the support clamp of FIG. 1.

BEST MODE OF PRACTICING INVENTION

Figure 3:
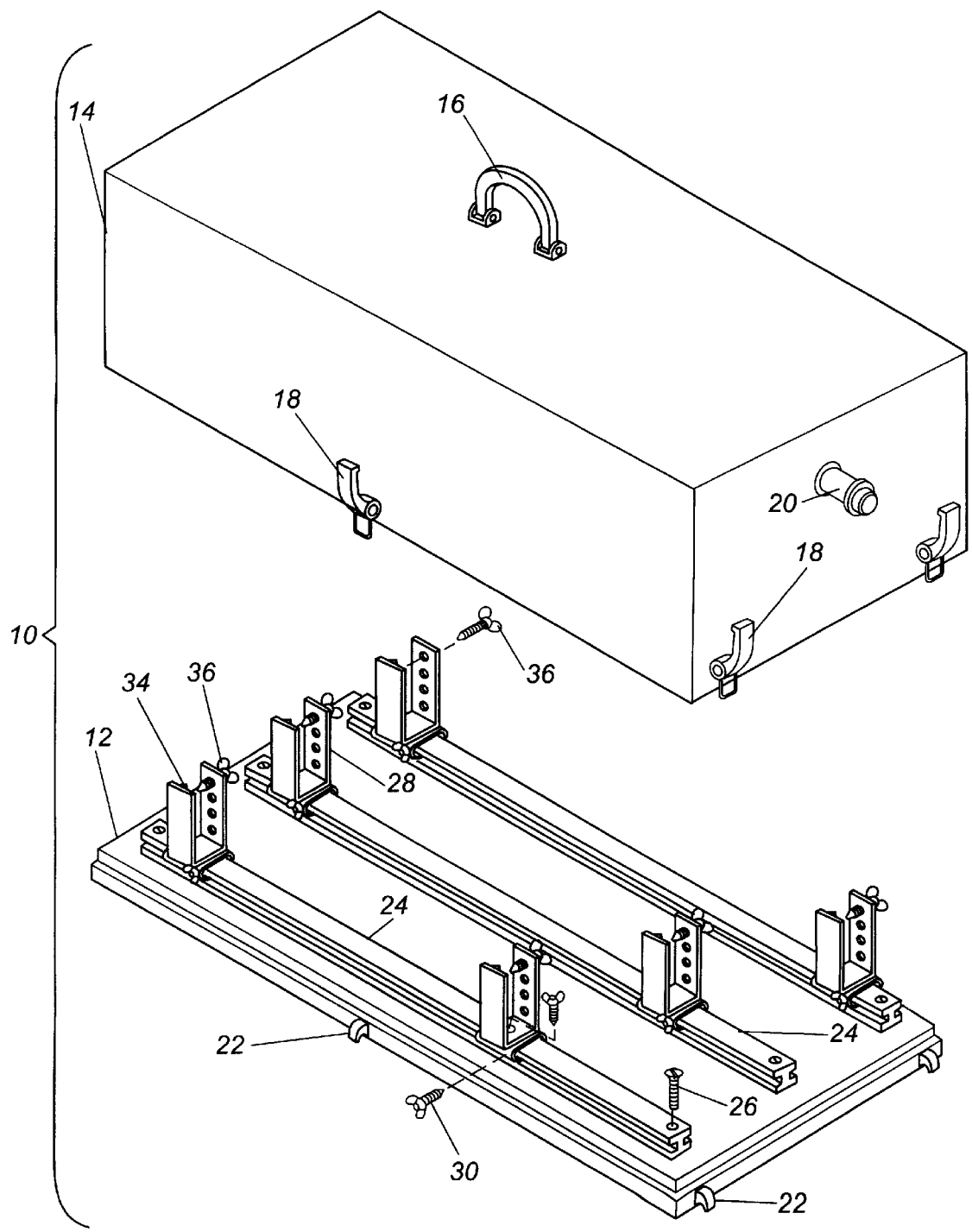
FIG. 3 is a partially exploded perspective drawing of a second embodiment of the evidence preserving carrier of the present invention.

In the description of the following figures, like numbers refer to like features in the embodiments of the invention:

FIG. 1 shows evidence-preserving container 10. The container has two main parts: container base 12 and container cover 14. Container cover 14 has carrying handle 16, cover clips 18, and fumigation vent 20. Container base 12 and cover 14 are preferably made of an opaque non-stick polymer, so that the fingerprint fixative will not permanently adhere to the inside of the cover and so that the contents of the container cannot be seen by on-lookers during transport. Container base 12, preferably made of similar material, has base clips 22 which, in use, join with cover clips 18 to connect container base 12 and container cover 14. Not illustrated, but important to the security of the container, and located so as to seal from water or dust from the connections between container cover 12 and container base 14, is a gasket. This gasket, preferably formed of elastomeric material, is preferably located along the lower edge of container cover 12. Mounted upon container base 12 are base supports 24 which are fastened to container base 12 by bar screws 26. Slidably mounted on base support bars 24 are support racks 28, each of which is comprised of two facing sides and a base, which are locked into the desired positions by rack thumb screws 30, which are tightened against support bars 24, to prevent movement of the support bars after they have been positioned to support the items which are placed into the container. Along one leg of each support rack 28 is a series of adjustment holes 32. On the opposite side of each support rack 28, is an elastomeric strip 34. FIG. 2 shows the configuration of elastomeric strip 34. The elastomeric strip faces the adjustment holes. Elastomeric strip 34 should have minimal contact with the item of evidence, and is preferred to form a point or have a minimal surface at the point of contact. Strip 34 has a triangular shape, as shown in simplified form in FIG. 2. The base of the triangle is affixed to the inner side and inner bottom side of support clamps 28 while the point of the triangle faces the item being secured. The surface could also be arcuate to yield a minimal contact surface. The position of elastomeric strips 34, the top portion above being visible in FIG. 1, are indicated by dashed lines on support racks 28. A series of individual elastomeric contact points, one located opposite each adjustment hole, could also be used instead of strips. The extension of elastomeric strip 34 across the bottom portion of support rack 28 further minimizes the area of the contact between the item secured and the support rack.

A series of support thumb screws 36, one per support clamp, and each having an elastomeric contact point 38 at its end, allow an item, such as a handgun, to be firmly held within the support racks. The elastomeric tip and elastomeric strip combination both hold the item securely and minimizes surface contact and chance of contamination between the gun and support bars. The number of support bars to be placed upon the base and of the support racks placed on those bars can be varied depending upon the size of the container desired, and the size item, and number of items to be carried. FIG. 1 shows three clamps each with three support racks, a combination that has proved to be small enough for convenience yet large enough to accommodate multiple guns of varying sizes.

In use at a crime scene, a handgun is picked up by a technician or officer wearing rubber gloves. The support racks have been positioned upon the support clamps so that the handle of the gun will be accepted within one support rack and the barrel of the handgun within another support rack. Using the support screws, the gun handle and gun barrel are each secured within the support racks. The evidence may be dusted for prints as in the prior art. The cover is latched onto the base for transport to the crime lab.

At the lab, a fixative glue for the fingerprint powder is blown into the container to coat the evidence. Prior to fixing, the dusting with powder may be performed at the lab, if not done at the crime scene. The cover is then removed and the item is examined for fingerprints that are no longer latent, but have become visible. Such fingerprints can then be lifted off the item for later evidential use. The advantage of fumigation within the case is that it avoids having to handle the item, while retaining the fixative material within the case. A first touching of the item to recover it from the crime scene and place it into some sort of container for transport is unavoidable. But every touching increases the risk that latent fingerprints will be obscured or damaged, or that the evidence will otherwise be contaminated. The container of the present invention, by allowing fumigation or dusting within the container, obviates multiple handling until fingerprints are obtained.

The "support clamps and thumbscrews" version show in FIG. 1 has been found the preferable design for securing and transporting handguns.

FIG. 3 shows a variation of the embodiment shown in FIG. 1: all numbered and identified parts are similar in each figure. Only the placement and spacing of the components has been varied so as to accommodate one or more rifles or shotguns.

Figure 4:
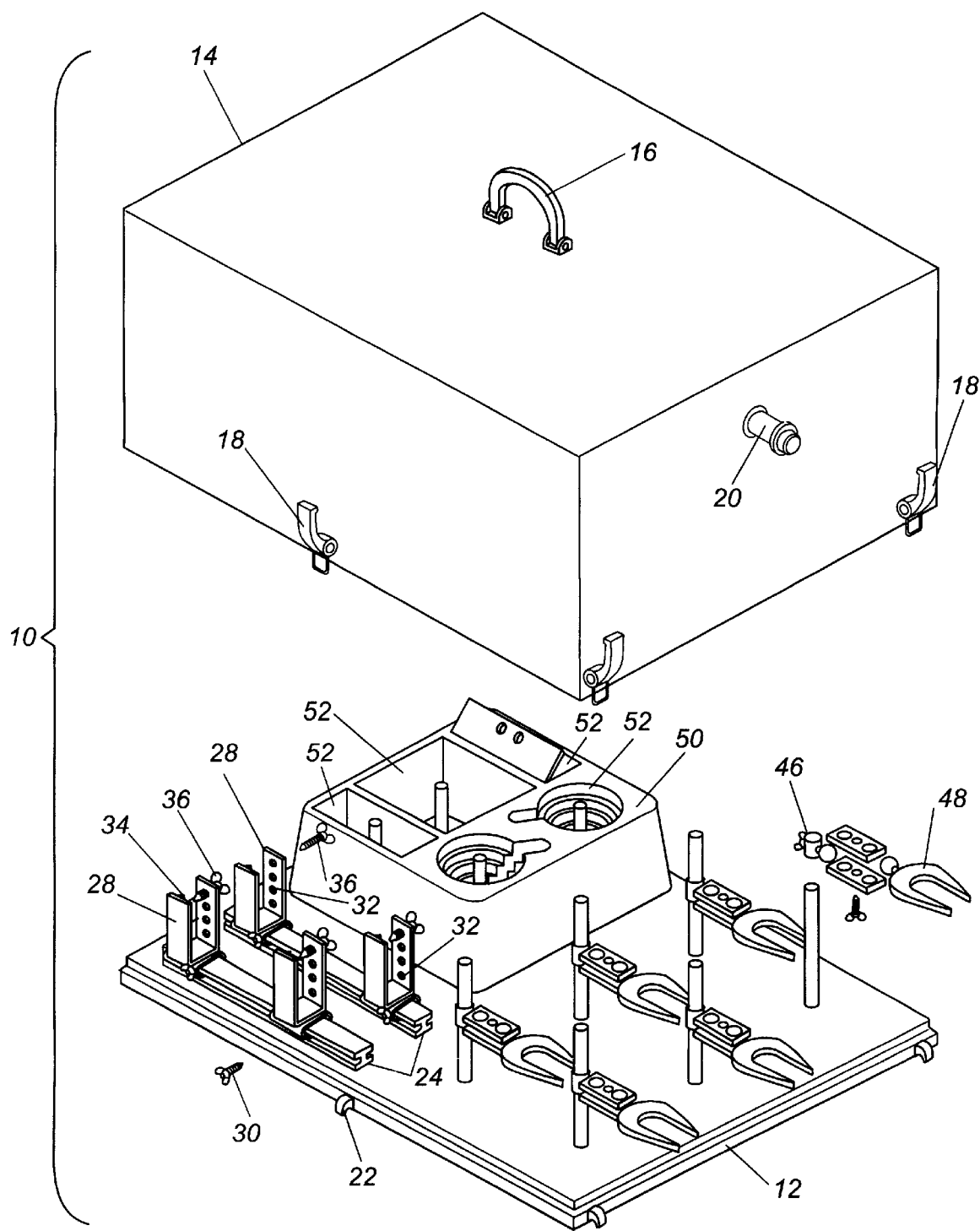
FIG. 4 is a partially exploded perspective drawing of a third embodiment of the evidence preserving carrier of the present invention.

FIG. 4 shows a variation of the present invention that accommodates, by use of a plurality of adjustable U-clamps and a storage compartment, a wider variety of items, especially smaller ones, than the embodiments shown in FIGS. 1 and 3. In FIG. 4, one portion of the container base 12 has the "support clamps and thumbscrews" version illustrated in FIG. 1. Two other types of means for securing an item within container 10 are show in FIG. 4: a plurality of post and U-clamp fixtures and a multi compartment storage unit. The "post and U-clamp" variation securing means is comprised off a plurality of removable rods 40 that have threaded ends 42 adapted to screw into sockets 44 formed or machined into container base 12. Movably attached to each rod 40 by means of clamp and screw fixture 46 is U-clamp 48. U-clamps 48 are preferably made of aluminum. On another section of container base 12 is located multi-compartment storage unit 50 which has formed therein several differently sized and configured storage compartments (generically 52). As in said with reference to FIG. 1, the number and placement of the various kinds of support means can be varied.

Other modifications of the evidence preserving carrier of the present invention will become apparent to those skilled in the art from an examination of the above patent specification and drawings. Therefore, other variations of the present invention may be made which fall within the scope of the following claims, even though such variations were not specifically discussed above.

The use of the container for the protection and subsequent treatment for latent fingerprints has been described when the item is a handgun, but, with appropriate adjustments to the securing means, or the selection of a different embodiment, items of evidence such as knives, blunt objects such as wrenches, bottles, personal effects, etc., would be similarly handled. In addition, the container is suitable for the transport of a any item that needs to be securely protected and its utility is not limited to its use for preserving and protecting an item to be treated for fingerprints.

What is claimed is:

1. A method of transporting and treating an item of evidence for latent fingerprints, comprising:
   a) taking a container, said container comprising a base portion and a cover portion which is releasably attached to said base portion, wherein at least one support rack is located within said container;
   b) securing at least one item inside the container and within the at least one support rack;
   c) dusting the at least one item contained within said container with fingerprint powder;
   d) securing the cover portion to the base portion of the container;
   e) transporting the container and the at least one item to a remote location; and
   f) applying a sufficient amount of fixative material to coat the at least one item secured within the container.

2. A method of transporting and then treating an item of evidence for latent fingerprints according to claim 1, wherein the at least one support rack located within the container comprises a multiplicity of support members which are removably attached to the base portion of the container, and a multiplicity of U-clamps, with each of said multiplicity U-clamps being adjustably closeable.

3. A method of transporting and then treating an item of evidence for latent fingerprints according to claim 1, wherein the container additionally comprises a closeable port on at least one side of the container, and wherein a sufficient amount of fixative material to coat the item secured within the container is introduced to the at least one item through said port.

4. A method of transporting and then treating an item of evidence for latent fingerprints according to claim 1, wherein the container is formed of opaque plastic which resists adherence of said fixative material to said opaque plastic.

5. A method of transporting and then treating an item of evidence for latent fingerprints according to claim 1, said base portion of the container further comprising a storage compartment having a multiplicity of storage cavities formed therein.

6. A method of transporting and then treating an item of evidence for latent fingerprints according to claim 1, further comprising at least one latch which removably attaches said base portion to said cover portion.

7. A method of transporting and then treating an item of evidence for latent fingerprints according to claim 1, wherein the at least one support rack comprises a multiplicity of screws and a series of threaded voids, with each of said voids admitting one of the multiplicity of screws, the depth of penetration of each of the screws within each of said threaded voids being variable by threading of each of said screws within each of said voids.

8. A method of transporting and then treating an item of evidence for latent fingerprints according to claim 1, wherein said at least one support rack comprises a multiplicity of screws, and wherein said multiplicity of screws has an elastomeric tip and, located upon said at least one support rack and facing each of said multiplicity of screws is an elastomeric contact point.

9. A method of transporting and then treating an item of evidence for latent fingerprints according to claim 1, wherein the container is formed of an opaque polymer which resists adherence of said fixative material to said opaque plastic.

10. A method of transporting and then treating an item of evidence for latent fingerprints comprising:

a) taking a container, said container comprising a base portion and a cover portion which is releasably attached to said base portion, wherein at least one support rack is located within said container;
   b) securing at least one item inside the container and within the at least one support rack;
   c) transporting the container and the at least one item to a remote location;
   d) dusting the at least one item contained within said container with fingerprint powder
   e) securing the cover portion to the base portion of the container; and
   f) applying a sufficient amount of fixative material to coat the at least one item secured within the container.

11. A method of transporting and treating an item of evidence for latent fingerprints according to claim 10, wherein the at least one support rack located within the container comprises a multiplicity of support members which are removably attached to the base portion of the container, and a multiplicity of U-clamps, with each of said multiplicity U-clamp being adjustably closeable.

12. A method of transporting and treating an item of evidence for latent fingerprints according to claim 10, wherein the container additionally comprises a closeable port on at least one side of the container, and wherein a sufficient amount of fixative material to coat the item secured within the container is introduced to the at least one item through said port.

13. A method of transporting and treating an item of evidence for latent fingerprints according to claim 10, wherein the container is formed of opaque plastic which resists adherence to said fixative material.

14. A method of transporting and treating an item of evidence for latent fingerprints according to claim 10, said base portion of the container further comprising a storage compartment having a multiplicity of storage cavities formed therein.

15. A method of transporting and treating an item of evidence for latent fingerprints according to claim 10, further comprising at least one latch which removably attaches said base portion to said cover portion.

16. A method of transporting and treating an item of evidence for latent fingerprints according to claim 10, wherein the at least one support rack comprises a multiplicity of screws and a series of threaded voids, with each of said voids admitting one of the screws, the depth of penetration of each of the screws within each of said threaded voids being variable by threading of each of said screws within each of said voids.

17. A method of transporting and treating an item of evidence for latent fingerprints according to claim 10, wherein said at least one support rack comprises a multiplicity of screws, and wherein said multiplicity of screws has an elastomeric tip and, located upon said at least one support rack and facing each of said multiplicity of screws is an elastomeric contact point.

18. A method of transporting and treating an item of evidence for latent fingerprints according to claim 10, wherein the container is formed of an opaque polymer which resists adherence to said fixative material.

\* \* \* \* \*